US010674989B2

(12) United States Patent
Watanabe et al.

(10) Patent No.: US 10,674,989 B2
(45) Date of Patent: Jun. 9, 2020

(54) RADIATION SYSTEM

(71) Applicant: Shimadzu Corporation, Kyoto (JP)

(72) Inventors: Shota Watanabe, Kyoto (JP); Isao Nakanishi, Kyoto (JP)

(73) Assignee: Shimadzu Corporation, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 16/137,034

(22) Filed: Sep. 20, 2018

(65) Prior Publication Data

US 2020/0093457 A1    Mar. 26, 2020

(51) Int. Cl.
*A61B 6/00* (2006.01)
*G16H 30/40* (2018.01)
*G16H 30/20* (2018.01)

(52) U.S. Cl.
CPC .............. *A61B 6/563* (2013.01); *A61B 6/566* (2013.01); *G16H 30/20* (2018.01); *G16H 30/40* (2018.01)

(58) Field of Classification Search
CPC ........ A61B 6/563; A61B 6/566; G16H 30/20; G16H 30/40

USPC ......................................................... 250/393
See application file for complete search history.

(56) References Cited

U.S. PATENT DOCUMENTS

2006/0176999 A1*  8/2006  Proano ................... A61B 6/563
                                                          378/91
2011/0051895 A1*  3/2011  Vogtmeier ............. A61B 6/032
                                                          378/92

FOREIGN PATENT DOCUMENTS

JP          2017164051 A  *  9/2017

* cited by examiner

*Primary Examiner* — David P Porta
*Assistant Examiner* — Gisselle M Gutierrez
(74) *Attorney, Agent, or Firm* — Muir Patent Law, PLLC

(57) ABSTRACT

The radiation system includes a radiation device, a computer, and a substrate configured to relay them. The substrate includes a video signal—Ethernet (registered trademark) conversion unit for converting a video signal from the computer into video data into an Ethernet (registered trademark) protocol and an X-ray imaging apparatus communication unit for transmitting the video data to the X-ray imaging apparatus by communications. The substrate and the radiation device are electrically insulated.

4 Claims, 6 Drawing Sheets

RADIATION SYSTEM

BACKGROUND OF THE INVENTION

Field of the Invention

The present invention relates to a radiation system provided with a radiation device, a computer, and a substrate relaying them.

Description of the Related Art

Conventionally, as this type of a radiation device, for example, there is a structure as shown in FIG. 6. As shown in FIG. 6, the radiation device 101 and the computer 201 arranged outside the radiation device 101 are electrically connected via cables 301. As shown in FIG. 6, the radiation device 101 is equipped with a local area network (LAN) port (hereinafter abbreviated as "LAN port") 102, a medical image transmitter 103, and a video signal receiver 104. Further, the computer 201 is also provided with a LAN port 202, a grabber board 203, and a graphic card 204. In the following description, an Ethernet (registered trademark) protocol will be described as an example of a communication protocol.

By electrically connecting the LAN port 102 of the radiation device 101 and the LAN port 202 of the computer 201 via an Ethernet (registered trademark) cable 302, an Ethernet (registered trademark) communication between the radiation device 101 and the computer 201 is performed. By electrically connecting the medical image transmitter 103 of the radiation device 101 and the grabber board 203 of the computer 201 via, for example, a cable 303 of the low voltage differential signal (LVDS: Low Voltage Differential Signaling) standard, a medical image signal is transmitted to the grabber board 203.

By electrically connecting the video signal receiver 104 of the radiation device 101 and the graphic card 204 of the computer 201 via a cable 304 of, for example, a digital visual interface (DVI: Digital Visual Interface) standard or a video graphics array (VGA: Video Graphics Array) standard, the video signal receiver 104 receives the video signal of (graphic card 204 of) the computer 201. In this manner, between the radiation device and the computer, a video signal of the computer, a signal converted into an Ethernet (registered trademark) protocol (Ethernet (registered trademark) signal), a signal for a medical image, and a synchronization signal are transferred.

There exists a non-electrically insulated connection like a DVI standard. As described above, since the radiation device and the computer are electrically connected, it is necessary to check the safety of the radiation device as a whole in order to change the model of the computer. Especially, in the case of a medical image, the rating is severe, so it is necessary to conduct a safety operation test and it is more necessary to confirm the safety.

SUMMARY OF THE INVENTION

Problems to be Solved by the Invention

However, as described above, it is necessary to confirm the safety of the radiation device as a whole, so there is a problem that the man-hour and cost (for performing the safety operation test) are high. Therefore, it is not easy to change the model of the computer.

The present invention has been made in view of the above circumstances, and aims to provide a radiation system used for connecting a radiation device which makes the man-hour and cost lower for confirming the safety.

Means for Solving the Problems

In order to attain such an object, the present invention has the following configuration.

That is, a radiation system according to the present invention includes a radiation device, a computer, and a substrate configured to relay the radiation device and the computer, wherein the substrate includes a conversion means for converting an electric signal from the computer into video data and a transmission means for transmitting the video data to the radiation device by communications, and wherein the substrate and the radiation device are electrically insulated.

Functions and Effects

According to the radiation system of the present invention, a radiation system includes a radiation device, a computer, and a substrate configured to relay the radiation device and the computer, wherein the substrate includes a conversion means for converting an electric signal from the computer into video data and a transmission means for transmitting the video data to the radiation device by communications, and wherein the substrate and the radiation device are electrically insulated. By communicating between the radiation device and the computer via the substrate, converting the electric signal from the computer to the video data by the conversion means, and transmitting the video data to the radiation device by communications, the radiation device can also receive the video data converted from the computer. Further, since the radiation device and the substrate are electrically insulated, by confirming the safety between the substrate and the computer when changing the model of the computer, compared with the case of confirming the safety of the entire radiation device, the man-hour and cost to confirm safety is reduced. As a result, it is possible to easily change the model of the computer.

In the above-described radiation system according to the present invention, the substrate may include a signal processing means for performing image processing on the electric signal from the computer or compressing the electric signal from the computer. Here, it should be noted that the "signal processing" means general image processing (for example, enlargement/reduction or extraction) related to an image, including processing of compressing the electric signal from the computer and is different from the image processing specific to the radiation device (i.e., image processing of the radiation image obtained with the radiation device). Further, since in the DVI standard, it is designed to transmit the uncompressed electric signal, the electric signal can be compressed by the signal processing means.

Further, in the radiation system according to the above-described inventions, it is preferable that the substrate further include a communication means for sending and receiving data between the computer and the radiation device. The "communication" here includes the transmission/reception between the substrate and the computer and transmission/reception between the substrate and the radiation device.

Further, in the radiation system further including the above-described communication means, it is preferable that the substrate include a signal arbitration means for arbitrating the video data converted by the conversion means from the electric signal from the computer, the data from the radiation device via the communication means, and the data from the computer via the communication means.

In this specification, the "signal arbitration" means controlling a transfer direction of a signal. In this case, by the signal arbitration, the radiation device can receive data from the computer via the communication means, including the video data converted by the conversion means, via a single cable and also can transmit data from the radiation device to the substrate and even to the computer via the same cable. As a result, the connection between the radiation device and the substrate is performed by only one cable, which can reduce the number of cables.

Effects of the Invention

According to the radiation system of the present invention, a radiation system includes a radiation device, a computer, and a substrate configured to relay the radiation device and the computer, wherein the substrate includes a conversion means for converting an electric signal from the computer into video data and a transmission means for transmitting the video data to the radiation device by communications, and wherein the substrate and the radiation device are electrically insulated. By confirming the safety between the substrate and the computer when changing the model of the computer, compared with the case of confirming the safety of the entire radiation device, the man-hour and cost to confirm safety is reduced. As a result, it is possible to easily change the model of the computer.

DETAIL DESCRIPTION OF THE EMBODIMENTS

EXAMPLE 1

Hereinafter, Example 1 of the present invention will be described with reference to the attached drawings.

Figure 1:
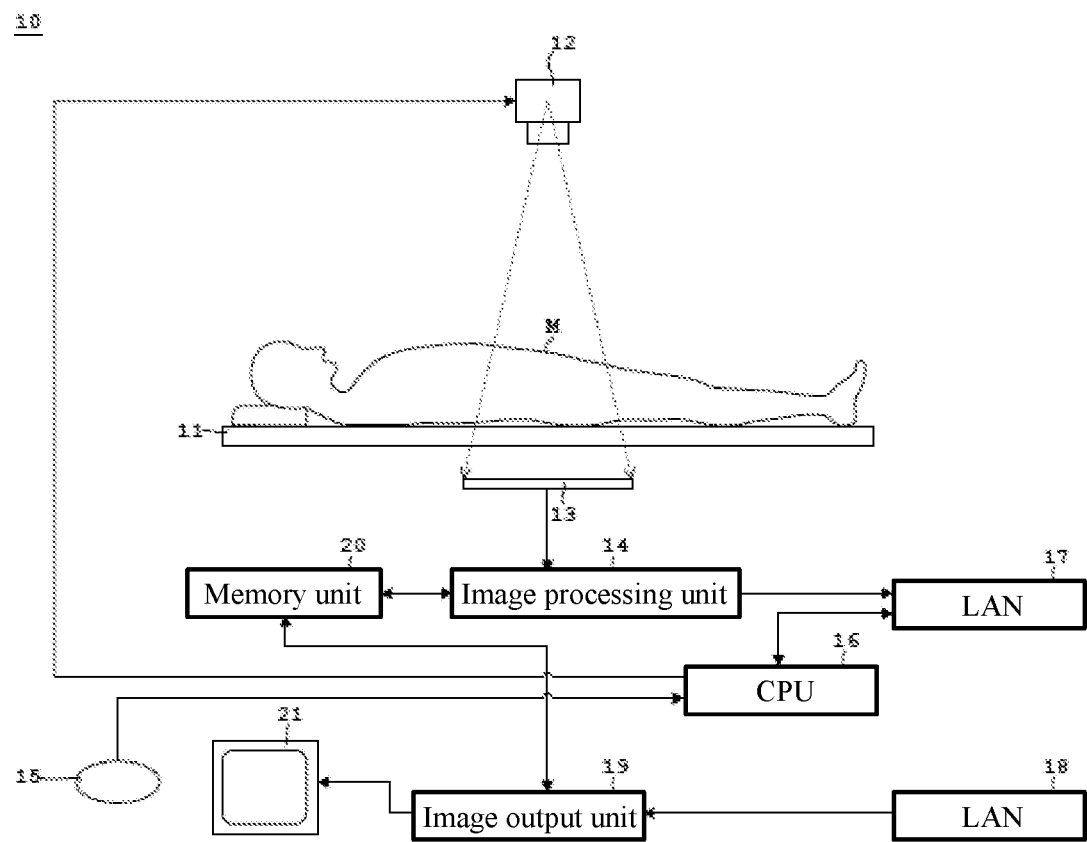
FIG. 1 is a block diagram of an X-ray imaging apparatus according to Example 1.
Figure 2:
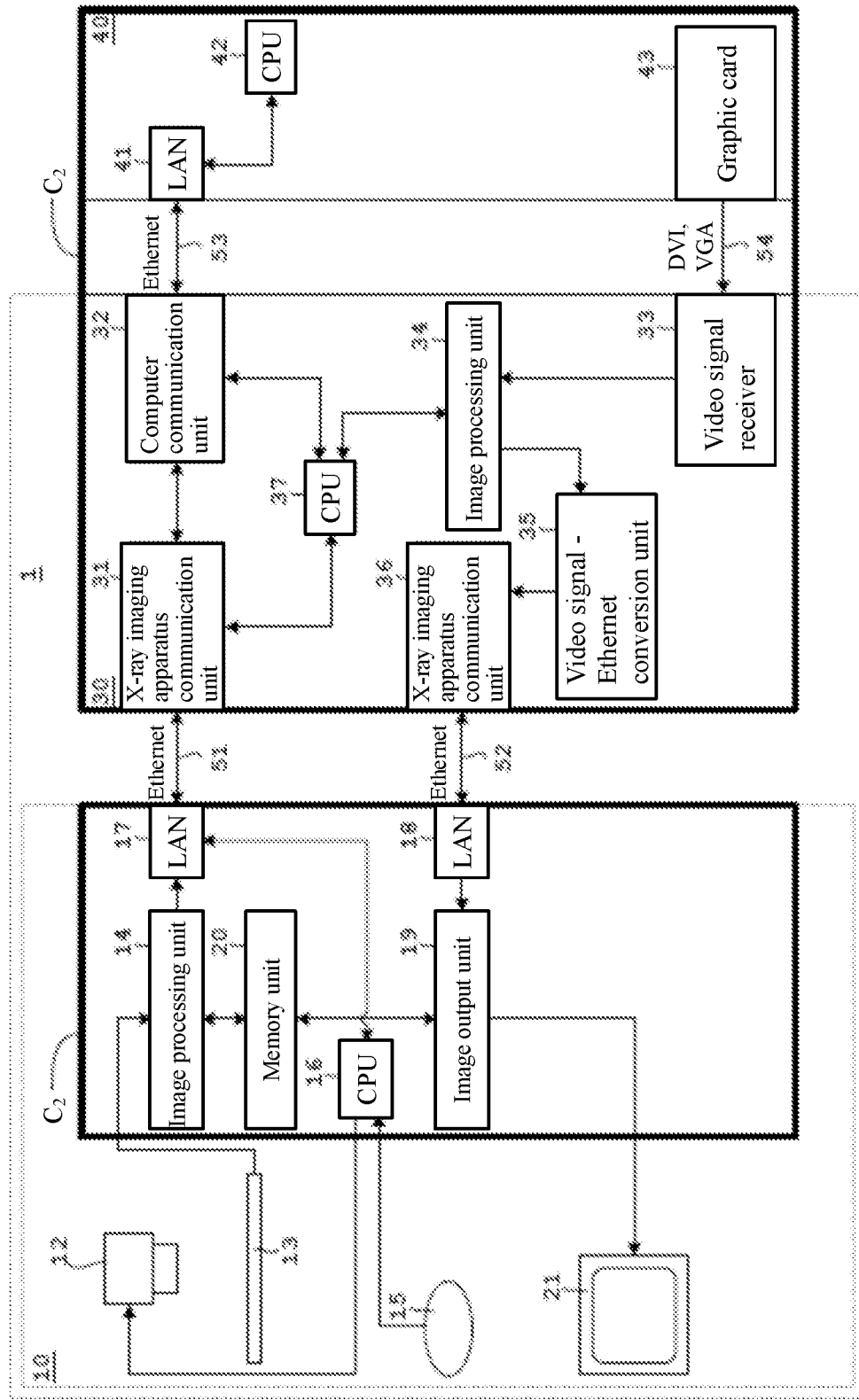
FIG. 2 is a block diagram of an X-ray imaging system according to Example 1 including an external computer.
Figure 3:
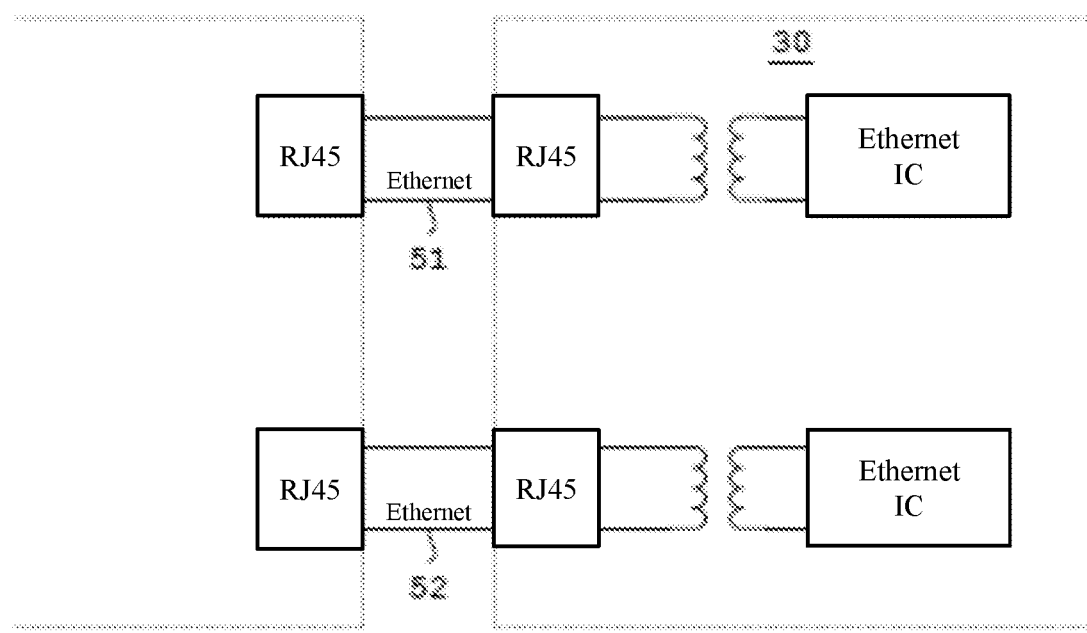
FIG. 3 is a circuit diagram of an RJ45 with a pulse transformer.

FIG. 1 is a block diagram of an X-ray imaging apparatus according to Example 1, FIG. 2 is a block diagram of an X-ray imaging system according to Example 1 including an external computer, and FIG. 3 is a circuit diagram of an RJ45 with a pulse transformer. Including Example 2 which will be described later, in Example 1, an X-ray imaging apparatus will be described as an example of a radiation device, and an X-ray imaging system will be described as an example of a radiation system.

As shown in FIG. 2, the X-ray imaging system 1 is provided with an X-ray imaging apparatus 10 (see also FIG. 1) and a substrate 30. The X-ray imaging apparatus 10 and the substrate 30 are electrically connected via Ethernet (registered trademark) cables 51 and 52. Further, the substrate 30 and the external computer 40 are electrically connected via an Ethernet (registered trademark) cable 53 and a cable 54 of a DVI standard or a VGA standard. The X-ray imaging system 1 corresponds to the radiation system in the present invention, the X-ray imaging apparatus 10 corresponds to the radiation device in the present invention, and the substrate 30 corresponds to the substrate in the present invention.

As shown in FIG. 1, the X-ray imaging apparatus 10 is provided with a top board 11 on which a subject M is placed, an X-ray tube 12 for irradiating X-rays toward the subject M, and a flat panel type X-ray detector (hereinafter, abbreviated as "FPD") 13 for detecting X-rays irradiated from the X-ray tube 2 and transmitted through the subject M.

Other than the above, as shown in FIG. 1 and FIG. 2, the X-ray imaging apparatus 10 is provided with an image processing unit 14 that performs image processing based on the X-rays detected by the FPD 13, an input unit 15 with which an operator, such as a technician, inputs data or instructions (commands), a central processing unit (hereinafter, abbreviated as "CPU") 16 that integrally control each component, an LAN port 17 that communicates with an X-ray imaging apparatus communication unit 31 (including transmission to the X-ray imaging apparatus communication unit 31, reception from the X-ray imaging apparatus communication unit 31) of a substrate 30, which will be described later, via an Ethernet (registered trademark) cable 51, with respect to the Ethernet (registered trademark) signal including the signal related to the X-ray image obtained by various image processing by the image processing unit 14, a LAN port 18 that receives a signal related to the X-ray image from the X-ray imaging apparatus communication unit 36 of the substrate 30, which will be described later, via the Ethernet (registered trademark) cable 52, an image output unit 19 that outputs a signal related to the X-ray image from the LAN port 18 as an X-ray image, a memory unit 20 that stores an X-ray image obtained by various image processing by the image processing unit 14 and stores the X-ray image output by the image output unit 19, and a display unit 21 that displays the X-ray image output by the image output unit 19.

Except for the top board 11, the X-ray tube 12, the FPD 13, the input unit 15, and the display unit 21, each component of the X-ray imaging apparatus 10 is stored in cabinet $C_1$ as shown in FIG. 2. Further, the substrate 30 and the computer 40, the Ethernet (registered trademark) cable 53 and the cable 54 connecting them are housed in the cabinet $C_2$ as shown in FIG. 2.

The substrate 30 is provided with an X-ray imaging apparatus communication unit 31 that communicates (Ethernet (registered trademark) communication) on the Ethernet (registered trademark) signal with the LAN port 17 of the X-ray imaging apparatus 10 via the Ethernet (registered trademark) cable 51, a computer communication unit 32 that communicates with the X-ray imaging apparatus communication unit 31 and Ethernet (registered trademark) communicates with the LAN port 41 of the computer 40 (to be described later) through the Ethernet (registered trademark) cable 53, a video signal receiver 33 that receives a video signal from a graphic card 43 of the computer 40, which will be described later, via the cable 54, an image processing unit 34 that performs image processing on the video signal of the computer 40 or compresses the video signal of the computer 40, a video signal—Ethernet (registered trademark) conversion unit 35 that converts the video signal of the computer 40 processed by the image processing unit 34 into an Ethernet (registered trademark) protocol, an X-ray imaging apparatus communication unit 36 that transmits a signal obtained by converting the video signal (signal related to an X-ray image) of the computer 40 via the video signal—Ethernet (registered trademark) conversion unit 35 into an Ethernet (Registered trademark) protocol to the LAN port 18 of the X-ray imaging apparatus 10 via the Ethernet (registered trademark) cable 52, and a CPU 37 for integrally controlling each component. The X-ray imaging apparatus communication unit 36 corresponds to the transmission means in the present invention, the X-ray imaging apparatus communication units 31 and 36, the computer communication unit 32, and the video signal receiver 33 correspond to the communication means in the present invention, the image processing unit 34 corresponds to the signal processing means in the present invention, and the video signal—Ethernet (registered trademark) conversion unit 35 corresponds to the conversion means in the present invention.

The external computer 40 is provided with a LAN port 41 for Ethernet (registered trademark) communicating with the computer communication unit 32 of the substrate 30 via the Ethernet (registered trademark) cable 53, a CPU 42 for controlling the LAN port 41, a graphic card 43 that outputs a video signal and transmits the video signal to the video signal receiver 33 of the substrate 30 via the cable 54.

The LAN port 17 of the X-ray imaging apparatus 10 and the X-ray imaging apparatus communication unit 31 of the substrate 30 are electrically connected via the Ethernet (registered trademark) cable 51. The LAN port 18 of the X-ray imaging apparatus 10 and the X-ray imaging apparatus communication unit 36 of the substrate 30 are electrically connected via the Ethernet (registered trademark) cable 52. The computer communication unit 32 of the substrate 30 and the LAN port 41 of the computer 40 are electrically connected via the Ethernet (registered trademark) cable 53. The video signal receiver 33 of the substrate 30 and the graphic card 43 of the computer 40 are electrically connected via the cable 54 (of a DVI standard or a VGA standard).

The image processing unit 14 of the X-ray imaging apparatus 10 is composed of the CPU described above. The image processing unit 14 may be configured by a programmable device or the like (for example, an FPGA (Field Programmable Gate Array) or a GPU (Graphics Processing Unit) in which the internal hardware circuit (e.g., logic circuit) can be changed according to program data. The input unit 15 of the X-ray imaging apparatus 10 is composed of a pointing device typified by, for example, a mouse, a keyboard, a joystick, a trackball, and a touch panel. The memory unit 20 of the X-ray imaging apparatus 10 is composed of a storage medium typified by, for example, a ROM (Read-only Memory) and a RAM (Random-Access Memory).

Each component of the substrate 30 is composed of a CPU mounted on the substrate 30, the above-described programmable device, an Ethernet (registered trademark) IC, which will be described later, or the like.

The specific communication protocol of Ethernet (registered trademark) is not particularly limited as being exemplified by a TCP/IP combining the transmission control protocol (TCP: Transmission Control Protocol) and the internet protocol (IP: Internet Protocol) and a user datagram protocol protocol (UDP: User Datagram Protocol).

The substrate 30 is insulated with connectors that connect the Ethernet (registered trademark) cables 51 and 52 wired from the X-ray imaging apparatus 10. In order to perform the insulation with respect to the substrate 30 using connectors that connect the Ethernet (registered trademark) cables 51 and 52 wired from the X-ray imaging apparatus 10, the RJ45 with a pulse transformer is adopted as the connector. As shown in FIG. 3, the RJ45 with a pulse transformer is composed of a transformer in which two coils are magnetically coupled, and this transformer is mounted on the substrate 30 (see also FIG. 2). One of the coils is connected to the RJ45 connector that connects the Ethernet (registered trademark) cables 51 and 52 (see FIG. 2), and the other coil is connected to the Ethernet (registered trademark) IC (X-ray imaging apparatus communication units 31 and 36 in FIG. 2).

An alternating current is passed through the primary coil (coil on the input side) to generate a magnetic field. The magnetic field is transferred to the secondary coil (output side coil) coupled with the mutual inductance, and again converted into a current. The current is output. In this way, it is possible to transmit a pulse signal composed of an alternating current while insulating by the primary coil and the secondary coil. When an Ethernet (registered trademark) signal is transmitted from the X-ray imaging apparatus 10 (see also FIG. 2) to the substrate 30, the coil connected to RJ45 connector is served as a primary coil, and the coil connected to the Ethernet (registered trademark) IC is serviced as a secondary coil. On the other hand, when the Ethernet (registered trademark) signal is transmitted from the substrate 30 to the X-ray imaging apparatus 10, the coil connected to the Ethernet (registered trademark) IC is served as a primary coil, and the coil connected to the RJ45 connector is served as a secondary coil.

In the X-ray imaging apparatus 10, insulation is performed on the substrate 30 with connectors that connect the cable (Ethernet (registered trademark) cable 51, 52 in FIG. 2) wired from the radiation device. However, as long as insulation is performed on the substrate with at least a connector that connects the cable wired from the radiation device, insulation may also be made to the substrate with a connector that connects the cable wired from the computer. For example, even in the case of the connector connecting the Ethernet (registered trademark) cable 53 wired from the computer 40 in FIG. 2, insulation is performed on the substrate 30. Further, although the insulation is performed between the X-ray imaging apparatus 10 and the substrate 30 by performing the insulation with a connector, the insulation may be performed between the X-ray imaging apparatus 10 and the substrate 30 by interposing a transformer in which two coils are magnetically coupled between the cables.

Returning to the description of FIG. 2, in this manner, in order to perform insulation with respect to the substrate 30 with the connectors connecting the Ethernet (registered trademark) cables 51 and 52 wired from the X-ray imaging apparatus 10, for the X-ray imaging apparatus communication units 31 and 36 for connecting with the X-ray imaging apparatus 10, an Ethernet (registered trademark) RJ45 connector is equipped with a pulse transformer capable of insulation. By adopting a pulse transformer that can be insulated, insulation is performed between the X-ray imaging apparatus 10 and the substrate 30. For signals other than the video signal of the computer 40, communication (Ethernet (registered trademark) communication) is performed using an Ethernet (registered trademark) protocol via the X-ray imaging apparatus communication unit 31 and the computer communication unit 32 on the substrate 30.

For the video signal of the computer 40, the video signal is converted into Ethernet (registered trademark) by the following procedure, and is transferred to the X-ray imaging apparatus 10.

1. The video signal receiver 33 on the substrate 30 receives the video signal from the graphic card 43 of the computer 40.

2. In the image processing unit 34 on the substrate 30, image processing, image compression, or both are performed on the received video signal as necessary.

3. With the video signal—Ethernet (registered trademark) conversion unit 35 on the substrate 30, the video signal is converted to the Ethernet (registered trademark) protocol.

4. For the signal (Ethernet (registered trademark) signal) converted into an Ethernet (registered trademark) protocol for a video signal, the X-ray imaging apparatus communication unit 36 on the substrate 30 Ethernet (registered trademark) communicates with (the LAN port 18 of) the X-ray imaging apparatus 10.

As described above, the video signal of the computer 40 received by the Ethernet (Registered trademark) communication is sent to the image output unit 19 as a signal related to the X-ray image. Then, the image output unit 19 outputs the signal related to the X-ray image as an X-ray image, the X-ray image is written and stored in the memory unit 20, and read out of the memory unit 20 when displaying the screen of the display unit 21 and send it to the display unit 21.

According to the radiation system (X-ray imaging system 1 in each Example) according to Example 1, including Example 2 which will be described later, the radiation system includes a radiation device (X-ray imaging apparatus 10 in each Example), a computer 40, and a substrate 30 for relaying them. The substrate 30 includes a conversion means (video signal—Ethernet (registered trademark) conversion unit 35 in each Example) for converting the electric signal (video signal in each Example) from the computer 40 into video data of an Ethernet (registered trademark) protocol, and a transmission means (X-ray imaging apparatus communication unit 36 in this Example 1) for transmitting the video data to the radiation device (X-ray imaging apparatus 10) by communications. The substrate 30 and the radiation device (X-ray imaging apparatus 10) are electrically insulated. By Ethernet (registered trademark) communicating between the radiation device (X-ray imaging apparatus 10) and the computer 40 via the substrate 30, converting the electric signal (video signal) from the computer 40 into video data of an Ethernet (registered trademark) protocol by the conversion means (video signal—Ethernet (registered trademark) conversion unit 35), and transmitting the video data to the radiation device (X-ray imaging apparatus 10) by the transmission means (X-ray imaging apparatus communication unit 36), the radiation device (X-ray imaging apparatus 10) can also receive the video data of the Ethernet (registered trademark) protocol converted from the computer 40. Further, since the radiation device (X-ray imaging apparatus 10) and the substrate 30 are electrically insulated, by confirming the safety between the substrate 30 and the computer 40 when changing the model of the computer 40, compared with the case of confirming the safety of the entire radiation device (X-ray imaging apparatus 10), the manhour and cost for confirming the safety can be reduced. As a result, it is possible to easily change the model of the computer 40.

Including Example 2 which will be described later, in this Example 1, in the radiation system (X-ray imaging system 1), the substrate 30 is provided with a signal processing means (image processing unit 34 in each Example) for performing image processing on an electric signal (video signal) from the computer 40 or compressing an electric signal (video signal) from the computer 40. As described in the section "Means for Solving the Problems", it should be noted that the "signal processing" as used herein means general image processing (for example, enlargement/reduction or extraction) related to images, including processing of compressing an electric signal (video signal) from the computer, and differs from the imaging processing specific to the radiation device (X-ray imaging system 1) (that is, the image processing of a radiation image obtained by the radiation device, image processing such as an offset correction, a gradation conversion and a grid elimination in the case of an X-ray image as in each Example). Further, since in the DVI standard, it is designed to transmit an uncompressed electric signal (video signal), so the electric signal (video signal) can be compressed by the signal processing means (image processing unit 34).

EXAMPLE 2

Next, Example 2 of the present invention will be described with reference to the attached drawings.

Figure 4:
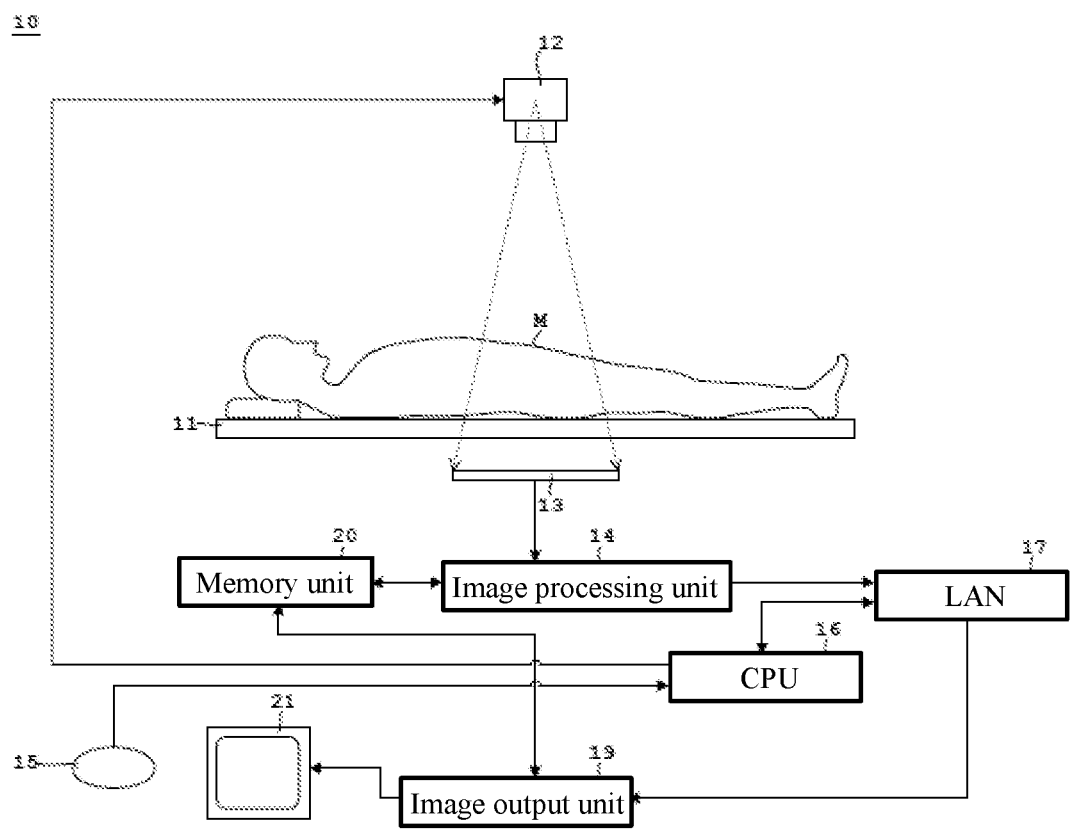
FIG. 4 is a block diagram of an X-ray imaging apparatus according to Example 2.
Figure 5:
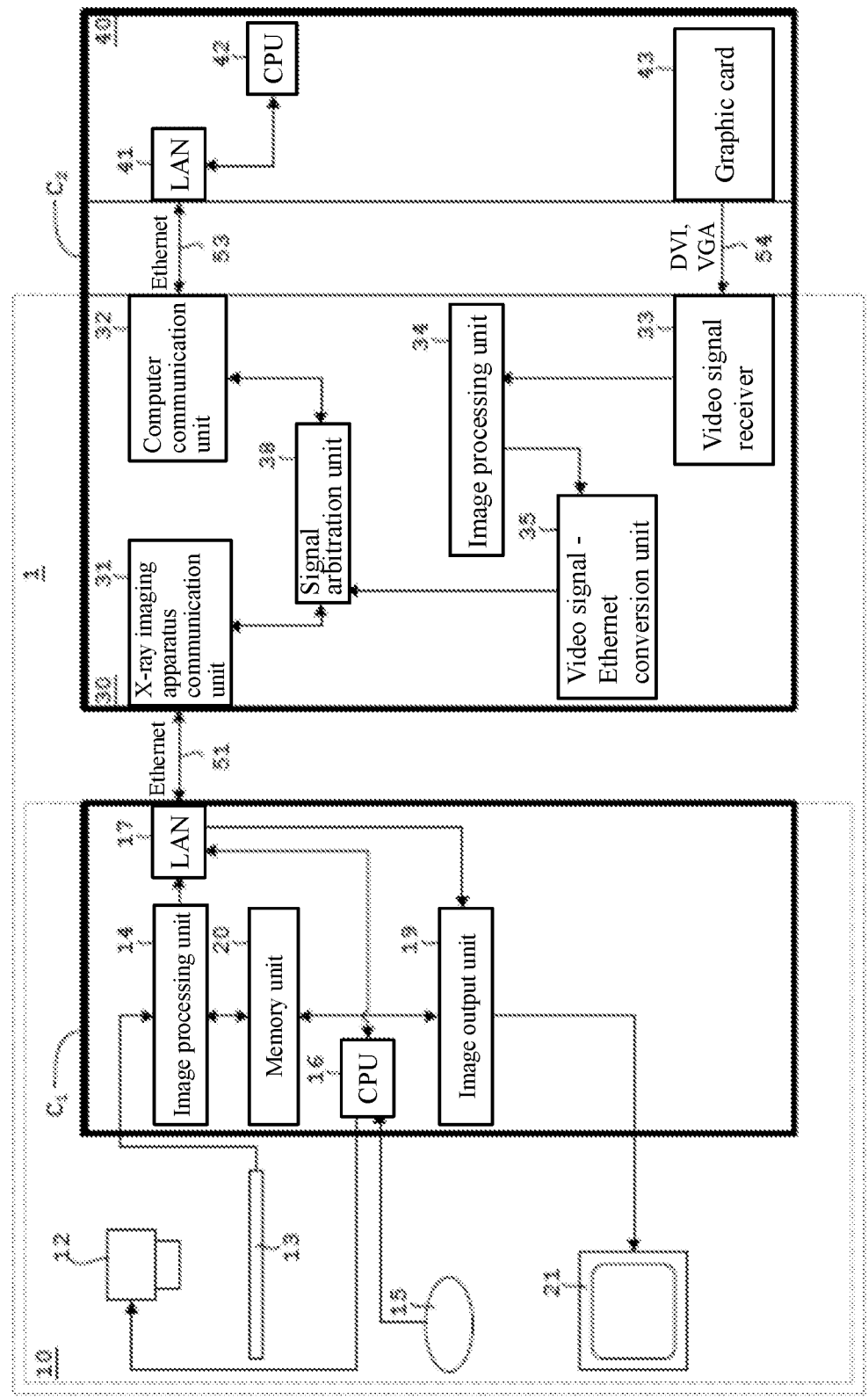
FIG. 5 is a block diagram of an X-ray imaging system according to Example 2 including an external computer.
Figure 6:
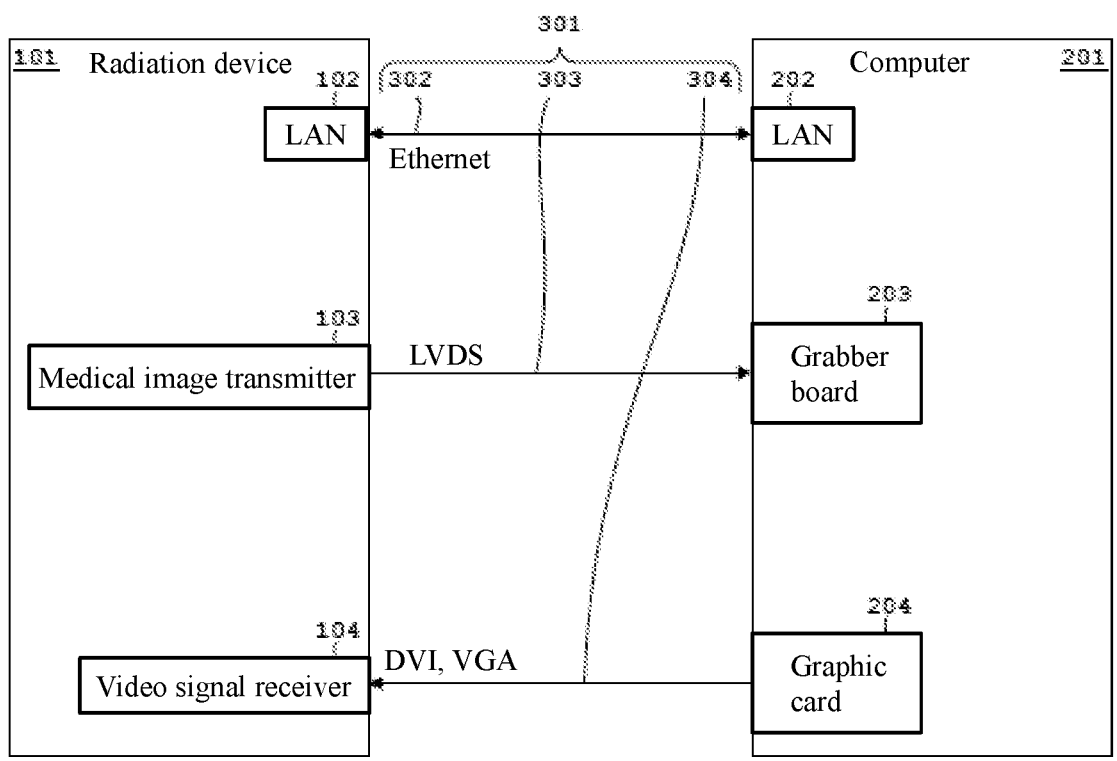
FIG. 6 is a block diagram of a conventional radiation device.

FIG. 4 is a block diagram of an X-ray imaging apparatus according to Example 2, and FIG. 5 is a block diagram of an X-ray imaging system according to Example 2 including an external computer. As for the configuration common to Example 1, the same reference numeral is allotted, and the detailed description thereof will be omitted.

In Example 1 described above, the X-ray imaging apparatus 10 is provided with two LAN ports 17 and 18 as shown in FIG. 1 and FIG. 2. On the other hand, in this Example 2, as shown in FIG. 4 and FIG. 5, the X-ray imaging apparatus 10 is provided with only one LAN port 17. Further, in Example 1 described above, as shown in FIG. 2, the substrate 30 is provided with two X-ray imaging apparatus communication units 31 and 36. On the other hand, in this Example 2, as shown in FIG. 5, the substrate 30 is provided with only one X-ray imaging apparatus communication unit 31.

Further, in Example 1 described above, as shown in FIG. 2, the LAN port 17 of the X-ray imaging apparatus 10 and the X-ray imaging apparatus communication unit 31 of the substrate 30 are electrically connected via the Ethernet (registered trademark) cable 51. The LAN port 18 of the X-ray imaging apparatus 10 and the X-ray imaging apparatus communication unit 36 of the substrate 30 are electrically connected via the Ethernet (registered trademark) cable 52. The X-ray imaging apparatus 10 and the substrate 30 are electrically connected via two Ethernet (registered trademark) cables 51 and 52. On the other hand, in this Example 2, as shown in FIG. 5, The LAN port 17 of the X-ray imaging apparatus 10 and the X-ray imaging apparatus communication unit 31 of the substrate 30 are electrically connected via the Ethernet (registered trademark) cable 51. The X-ray imaging apparatus 10 and the substrate 30 are electrically connected via only one Ethernet (registered trademark) cables 51.

In this Example 2, as shown in FIG. 4 and FIG. 5, the LAN port 17 of the X-ray imaging apparatus 10 is connected to the image processing unit 14, the CPU 16, and the image output unit 19. In addition, as shown in FIG. 5, the substrate 30 is provided with a signal arbitration unit 38 that arbitrates signals. The signal arbitration unit 38 corresponds to the signal arbitration means in the present invention.

The signal arbitration unit 38 is configured by a switching hub. The signal arbitration unit 38 is connected to an X-ray imaging apparatus communication unit 31, a computer communication unit 32, and a video signal—Ethernet (registered trademark) conversion unit 35. Note that the illustration of the CPU 37 is omitted.

For signals other than the video signal of the computer 40 in this Example 2, communication (Ethernet (registered trademark) communication) is performed using an Ethernet (registered trademark) protocol via the X-ray imaging apparatus communication unit 31, the signal arbitration unit 38, and the computer communication unit 32 on the substrate 30.

In this Example 2, for the video signal of the computer 40, the video signal is converted into Ethernet (registered trademark) by the following procedure, and is transferred to the X-ray imaging apparatus 10.

1. The video signal receiver 33 on the substrate 30 receives the video signal from the graphic card 43 of the computer 40.

2. In the image processing unit 34 on the substrate 30, image processing, image compression, or both are performed on the received video signal as necessary.

3. With the video signal—Ethernet (registered trademark) conversion unit 35 on the substrate 30, the video signal is converted to the Ethernet (registered trademark) protocol.

4. For the signal (Ethernet (registered trademark) signal) converted into an Ethernet (registered trademark) protocol for a video signal, the X-ray imaging apparatus communication unit 31 on the substrate 30 Ethernet (registered trademark) communicates with (the LAN port 17 of) the X-ray imaging apparatus 10 via the signal arbitration unit 38.

Thus, in the signal arbitration unit 38, the signal (Ethernet (registered trademark) signal) obtained by converting the video signal of the computer 40 into an Ethernet (Registered trademark) protocol, the Ethernet (registered trademark) signal from the X-ray imaging apparatus 10, and the Ethernet (registered trademark) signal from the computer 40 are arbitrated.

As for the main functions and effects in this Example 2 and the functions and effects in cases where the signal processing means (the image processing unit 34 in each Example) is provided, they are the same as those of Example 1 described above, the description will be omitted.

As in this Example 2, in the radiation system (X-ray imaging system 1 in each Example), it is preferable that the substrate 30 be provided with a signal arbitration means (the signal arbitration unit 38 in this Example 2) which arbitrates the video data (video signal in each Example) of the Ethernet (registered trademark) protocol converted from an electric signal from the computer 40 with a conversion means (video signal—Ethernet (registered trademark) conversion unit 35 in each Example), the data (an Ethernet (registered trademark) signal in each Example) via the radiation means (X-ray imaging apparatus 10 in each Example) via a communication means (X-ray imaging apparatus communication unit 31 in this Example 2), and the data (Ethernet (registered trademark) signal in each Example) from the computer 40 via the communication means (the computer communication unit 32 in each Example).

As also described in the section "Means for Solving the Problem", in the present specification, the "signal arbitration" means to control the transfer direction of a signal. In this case, by the signal arbitration, including video data of the Ethernet (registered trademark) protocol converted by the conversion means (video signal—Ethernet (registered trademark) conversion unit 35), the radiation device (X-ray imaging system 1) can receive the data (Ethernet (registered trademark) signal) from the computer via the communication means (computer communication unit 32) via a single cable (Ethernet (Registered trademark) cable 51 shown in FIG. 5), and it is possible to transmit data (Ethernet (registered trademark) signal) from the radiation device (X-ray imaging system 1) to the substrate 30 and further to the computer 40 via the same Ethernet (registered trademark) cable 51. As a result, only one Ethernet (Registered trademark) cable 51 is connected between the radiation device (X-ray imaging system 1) and the substrate 30, thereby reducing the number of cables.

The present invention is not limited to the aforementioned embodiment, and can be modified as follows.

(1) In each Example described above, an X-ray imaging apparatus is described as an example of a radiation device, and an X-ray imaging system is described as an example of a radiation system, but the present invention may be applied to a radiation ($\alpha$ ray, $\beta$ ray, and $\gamma$ ray, etc.) device other than X-rays.

(2) In each Example described above, the present invention is applied to imaging, but it may be configured such that a plurality of projection data is sequentially acquired by irradiating radiation (X-rays in each Example) with a weaker dose than in imaging, and it may be applied to fluoroscopy in which the projection data (moving image) is displayed in real time.

(3) In each Example described above, the present invention is applied to a medical X-ray imaging apparatus/X-ray imaging system for imaging a subject such as a human body or a small animal, but may be applied to a radiation device/radiation system for industrial or industrial use that fluoroscopes or image a subject such as a substrate.

(4) In each of the above-described Examples, the imaging mode is as shown in FIG. 1 and FIG. 4. However, as exemplified by tomographic imaging such as CT (Computed Tomography) imaging and tomosynthesis, the fluoroscopic/imaging mode is not particularly limited.

(5) In each Example described above, the substrate is provided with a signal processing means (image processing unit 34 in each Example) for performing image processing on an electric signal (video signal) from the computer or compressing an electric signal (video signal) from the computer. In cases where it is not necessary to compress the electric signal (video signal) of the computer by sending a compressed electric signal (video signal) with a standard other than the DVI standard, or in cases where it is not necessary to perform general image processing (for example, enlargement/reduction or segmentation) on the image, it is not always necessary to provide a signal processing means (image processing unit 34).

(6) In each Example described above, an Ethernet (registered trademark) protocol is exemplified as a communication protocol, but it is not particularly limited as long as it is a communication protocol that is normally used.

DESCRIPTION OF REFERENCE SYMBOLS

1: X-ray imaging system
10: X-ray imaging apparatus
30: substrate
31, 36: X-ray imaging apparatus communication unit
32: computer communication unit
34: image processing unit
35: video signal—Ethernet (registered trademark) conversion unit
38: signal arbitration unit
51 to 53: Ethernet (registered trademark) cable

The invention claimed is:

1. A radiation system comprising:
a radiation device;
a computer;

a substrate configured to relay communications between the radiation device and the computer, the substrate having a processor;

a first communication cable extending between the radiation device and the substrate; and a second communication cable extending between the substrate and the computer, wherein the processor is configured to convert an electric signal from the computer into video data and to transmit the video data to the radiation device via the first communication cable, wherein the computer and the substrate are interconnected with the second communication cable that does not maintain electrical insulation between the computer and the substrate and are configured to communicate via the second communication cable with a standard for video transmission, and wherein the processor and the radiation device are electrically insulated from each other.

2. The radiation system as recited in claim 1, wherein the substrate includes signal processing means for performing image processing on the electric signal from the computer or compressing the electric signal from the computer.

3. The radiation system as recited in claim 1, wherein the substrate further includes communication means for sending and receiving data to and from the computer and the radiation device via the first and second communication cables.

4. The radiation system as recited in claim 3, wherein the substrate includes signal arbitration means for arbitrating the video data converted by the processor from the electric signal from the computer, the data from the radiation device via the communication means, and the data from the computer via the communication means.

* * * * *